US012128540B2

(12) United States Patent
Talal

(10) Patent No.: US 12,128,540 B2
(45) Date of Patent: Oct. 29, 2024

(54) QUICK RELEASE MECHANISM

(71) Applicant: Sibghat Talal, Lake Hopatcong, NJ (US)

(72) Inventor: Sibghat Talal, Lake Hopatcong, NJ (US)

( * ) Notice: Subject to any disclaimer, the term of this patent is extended or adjusted under 35 U.S.C. 154(b) by 535 days.

(21) Appl. No.: 17/590,873

(22) Filed: Feb. 2, 2022

(65) Prior Publication Data

US 2024/0326229 A1    Oct. 3, 2024

(51) Int. Cl.
*B25G 3/16* (2006.01)
*B23B 31/113* (2006.01)
*A61B 1/247* (2006.01)
*A61C 3/00* (2006.01)

(52) U.S. Cl.
CPC .............. *B25G 3/16* (2013.01); *B23B 31/113* (2013.01); *A61B 1/247* (2013.01); *A61C 3/00* (2013.01); *B23B 2240/04* (2013.01); *Y10T 279/17888* (2015.01)

(58) Field of Classification Search
CPC ..... Y10T 279/17351; Y10T 279/17444; Y10T 279/17888; B25G 3/16; B23B 31/113; B23B 2240/04; A61B 1/247; A61C 3/00
See application file for complete search history.

(56) References Cited

U.S. PATENT DOCUMENTS

| 111,265 | A | * | 1/1871 | Shoemaker | ........... | E21B 10/633 |
| | | | | | | 175/413 |
| 238,950 | A | * | 3/1881 | Miller | ..................... | A61C 1/141 |
| | | | | | | 279/93 |
| 552,625 | A | * | 1/1896 | Speakman | ............... | A61C 3/06 |
| | | | | | | 279/93 |
| 4,407,045 | A | | 10/1983 | Boothe | | |
| 4,420,860 | A | | 12/1983 | Chamuel | | |
| 5,634,534 | A | | 6/1997 | Kanai et al. | | |
| 5,658,087 | A | | 8/1997 | Butkovich et al. | | |
| 6,126,359 | A | * | 10/2000 | Dittrich | ..................... | B25G 3/04 |
| | | | | | | 403/325 |
| 6,467,136 | B1 | | 10/2002 | Graham | | |
| 7,448,823 | B2 | | 11/2008 | Silva | | |
| 7,523,528 | B2 | | 4/2009 | Carnevali | | |
| 7,726,998 | B2 | | 6/2010 | Siebens | | |
| 8,106,372 | B2 | * | 1/2012 | Powers | ..................... | G21F 5/015 |
| | | | | | | 250/507.1 |

(Continued)

*Primary Examiner* — Eric A. Gates
*Assistant Examiner* — Reinaldo A Vargas Del Rio
(74) *Attorney, Agent, or Firm* — Michael J. Feigin, Esq.; Feigin and Fridman LLC

(57) ABSTRACT

A quick release mechanism includes a male member including a locking pin, a female member including a cavity for receiving the male member, a locking joint on the female member including a longitudinal bore for receiving the male member, a longitudinal slit for receiving the locking pin, and a locking recess for capturing the locking pin, a spring within the cavity for securing the locking pin within the locking recess, and a bearing enabling rotation of the male member within the cavity. The male member engages the female member by guiding the locking pin into the slit and compressing the spring until the locking pin is released from the slit into the cavity. The locking pin is then able to shift into the locking recess by rotating the male member. The spring exerts a force onto the male member to maintain the locking pin within the locking recess.

16 Claims, 9 Drawing Sheets

(56) References Cited

U.S. PATENT DOCUMENTS

| | | |
|---|---|---|
| RE45,684 E | 9/2015 | Jones et al. |
| 9,884,413 B2 | 2/2018 | Patterson et al. |
| 2003/0145441 A1 | 8/2003 | Andersson et al. |

* cited by examiner

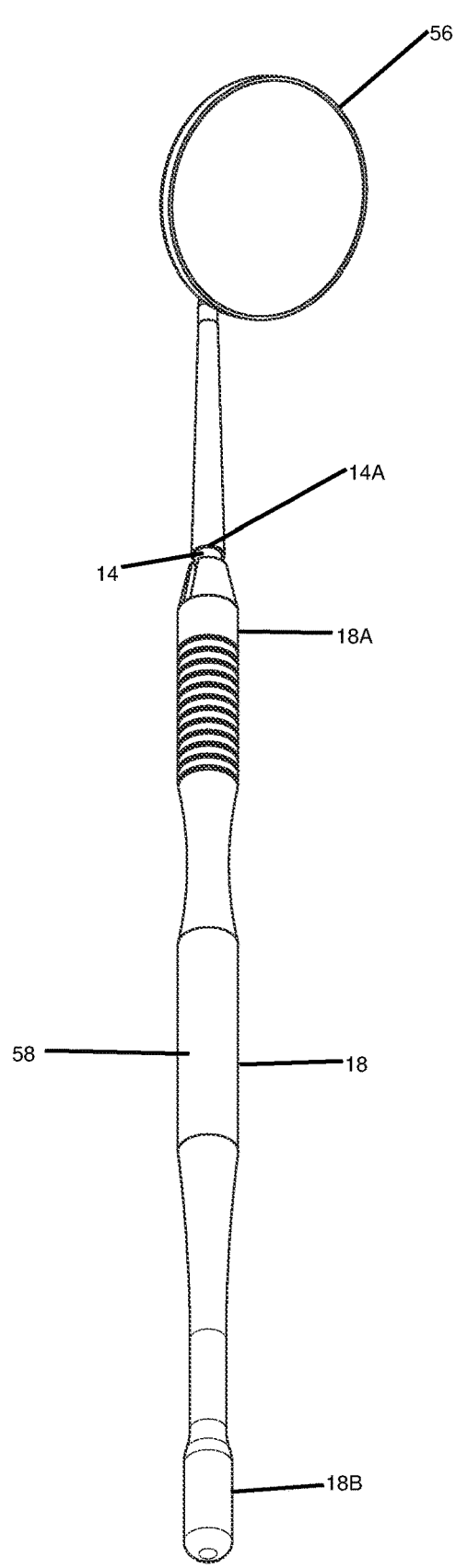
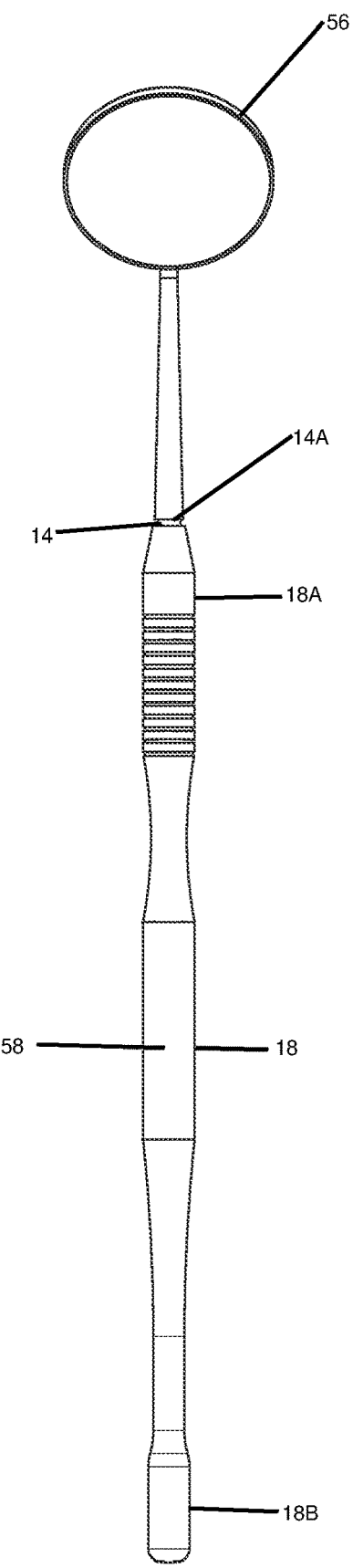
FIG. 7A
FIG. 7B

QUICK RELEASE MECHANISM

FIELD OF THE DISCLOSED TECHNOLOGY

The disclosed technology relates generally to quick release mechanisms. More specifically, the disclosed technology relates to a quick release mechanism including removably engageable female and male members for the quick interchangeability of dental tools.

BACKGROUND OF THE DISCLOSED TECHNOLOGY

Quick-release mechanisms have been commonplace for many years. These quick-release mechanisms allow for rapid connection (or disconnection) of two different objects without the need for specialized tools. While common applications of quick-release devices are for the securing of a bicycle wheel to the fork or frame of the bicycle, quick release devices are also used for other applications, such as pens for ejecting and retract the writing tip and cameras for locking and releasing SD cards.

While various types of quick-release retention systems have been devised, the most commonly used of these devices includes a push-latch system. Push-latch systems work by influencing a spring-biased latch to follow a track including a unique geometry. The latch engages the track in a first push stroke and disengages the latch on a second push stroke by utilizing spring forces.

Unfortunately, these conventional quick-release mechanism pose problems. One problem is that the system is entirely dependent upon the latch, which often time break or lose their spring force. Another problem is that if the geometrical track is flawed or gets compromised somehow, the latch will not be able to latch and release.

It would therefore be desirable to have a quick-release mechanism that it not dependent on a spring biased latch and the unique geometry of an embedded track.

SUMMARY OF DISCLOSED TECHNOLOGY

The disclosed technology provides a quick release mechanism including a male member having an elongated shaft and a locking pin, a female member including a substantially counterbored cavity for receiving the male member, a locking joint for receiving the elongated shaft and the locking pin within the female member, a spring for securing the locking pin within the locking joint, and a bearing for enabling rotation of the elongated shaft within the counterbored cavity with respect to the spring. The elongated shaft includes a first end, a second end, the first end opposite the second end, and a longitudinal length extending between the first end and the second end, the elongated shaft including a locking pin protruding substantially orthogonally outwardly from the elongated shaft. The female member also includes a first end, a second end, the first end opposite the second end, the first end including a perimeter edge defining an opening providing access to the counterbored cavity, the counterbored cavity comprising a first bore with a bottom surface including a second bore. The locking joint is attached to the first end of the female member and includes a body having a first end, a second end, the first end opposite the second end, a first side, a second side, the first side opposite the second side, an exterior surface, a longitudinal bore extending from the first end to the second end, an interior surface within the longitudinal bore, a longitudinal slit disposed on the first side, the longitudinal slit extending longitudinally from the first end to the second end and transversely from the exterior surface to the interior surface, and a collar protruding outwardly from the exterior surface of the body.

The longitudinal bore is configured to receive the male member therethrough while the longitudinal slit is configured to receive the locking pin therethrough. The longitudinal bore defines an entry point at the first end and an exit point at the second end. The collar engage the perimeter edge of the first end of the female member to maintain the locking joint at the first end of the female member. The second end of the body is positioned within the counterbored cavity of the female member against the bottom surface of the counterbored cavity. The second side of the body includes a length greater than a length of the first side such that the second end includes a first peripheral edge on the first side and a second peripheral edge on the second side that is stepped with respect to the first peripheral edge. The locking joint further includes a locking recess disposed between the first peripheral edge and the second peripheral edge. The locking recess is configured to receive the locking pin therein. The spring is disposed in the second bore of the counterbored cavity of the female member. The spring biased toward the first end of the female member to secure the locking pin within the locking recess. The bearing is positioned on the spring within the counterbored cavity and configured to contact the second end of the elongated shaft and enable rotation of the elongated shaft within the counterbored cavity with respect to the spring. The male member removably engages the female member by inserting the elongated shaft into the entry point and the locking pin into the longitudinal slit and compressing the spring until the elongated shaft exits the exit point and the locking pin is released from the longitudinal slit into the counterbored cavity enabling shifting of the locking pin along the first peripheral edge until the locking pin engages the locking recess. The spring exerts a restoring force onto the second end of the elongated shaft via the bearing to maintain the locking pin within the locking recess.

In embodiments, the male member is inserted into the female member by aligning the locking pin with the longitudinal slit of the locking joint at the entry point and guiding the elongated shaft into the longitudinal bore and the locking pin into the longitudinal slit toward the second end of the female member.

In some embodiments, the locking pin is released from the longitudinal slit within the first bore of the counterbored cavity of the female member by guiding the locking pin along the longitudinal slit toward the second end of the female member until the locking pin reaches the first peripheral edge of the second end of the locking joint and exits the longitudinal slit at the exit point enabling transverse movement within the first bore along the first peripheral edge toward the locking recess.

In other embodiments, as the elongated shaft is driven further into the longitudinal bore of the locking joint and the counterbored cavity of the female member, the second end of the elongated shaft engages the bearing which compresses the spring in the second bore toward the second end of the female member, thereby generating a potential restoring force in the spring that is biased toward the first end of the female member.

In embodiments, once the locking pin is released from the longitudinal slit, the locking pin engages the locking recess by rotating the elongated shaft to shift the locking pin toward the second peripheral edge until the locking pin engages the locking recess and then releasing the elongated shaft.

In some embodiments, when the elongated shaft is released, the spring exerts its restoring force on the elongated shaft and the locking pin toward the first end of the female member, thereby securing the pin within the locking recess and locking the male member inside of the female member.

In other embodiments, the spring remains partially compressed when the locking pin is within the locking recess, thereby continuously exerting its restoring force on the locking pin and maintaining the locking pin within the locking recess.

In embodiments, the male member is released from the female member by driving the elongated shaft back toward the second end of the female member to compress the spring and disengage the locking pin from the locking recess, rotating the elongated shaft to shift the locking pin back along the first peripheral edge to align the locking pin with the longitudinal slit of the locking joint, and guiding the locking pin back along the longitudinal slit toward the first end of the locking joint until the locking pin exits the locking joint.

In some embodiments, the first bore is coaxial with the second bore and includes a diameter larger than a diameter of the second bore.

In other embodiments, the second peripheral edge is the only part of the second end of the locking joint that contacts the bottom surface of the counterbored cavity.

In certain embodiments, the collar tapers in diameter toward the first end of the locking joint.

In embodiments, the locking joint further includes a second locking recess disposed between the first peripheral edge and the second peripheral edge, the second locking recess opposite the first locking recess.

In some embodiments, the diameter of the elongated shaft is smaller than the diameter of the second bore of the counterbored cavity enabling the elongated shaft to slide into the second bore when compressing the spring.

In other embodiments, the longitudinal bore of the locking joint is substantially equal in diameter to the second bore of the counterbored cavity.

In embodiments, the first end of the elongated shaft of the male member includes a dental tool selected from the group consisting of a mouth mirror, sickle probe, scaler, saliva ejector, suction device, dental drill, and dental syringe.

In some embodiments, the female member includes an elongated handle extending between the first end of the female member and the second end of the female member.

"Counterbore" refers to "a cylindrical substantially flat-bottomed hole that enlarges another coaxial hole." "Equilibrium position" refers to "the position of an item, such as a spring, in which an external force has not acted on it, i.e., has not been stretched or compressed." "Potential restoring force" refers to "the force necessary to return a compressed or stretched item, such as a spring, back to its equilibrium position." "Transverse" refers to "from side to side or rotation about a plane."

Any device or step to a method described in this disclosure can comprise or consist of that which it is a part of, or the parts which make up the device or step. The term "and/or" is inclusive of the items which it joins linguistically and each item by itself. "Substantially" is defined as "at least 95% of the term being described" and any device or aspect of a device or method described herein can be read as "comprising" or "consisting" thereof.

BRIEF DESCRIPTION OF THE DRAWINGS

FIG. 7A shows a perspective view of the quick release mechanism according to one embodiment of the present disclosed technology.

FIG. 7B shows a front view of the quick release mechanism according to one embodiment of the present disclosed technology.

DETAILED DESCRIPTION OF EMBODIMENTS OF THE DISCLOSED TECHNOLOGY

The present disclosed technology provides a quick release mechanism that facilitates the quick engagement and disengagement of discrete components to enable efficient interchangeability of dental tools on one handle. The quick release mechanism includes a male member including a locking pin, a female member including a cavity for receiving the male member, a locking joint on the female member including a longitudinal bore for receiving the male member, a longitudinal slit for receiving the locking pin, and a locking recess for capturing the locking pin, a spring within the cavity for securing the locking pin within the locking recess, and a bearing enabling rotation of the male member within the cavity. The male member engages the female member by guiding the locking pin into the slit and compressing the spring until the locking pin is released from the slit into the cavity. The locking pin is then able to shift into the locking recess by rotating the male member. The spring exerts a force onto the male member to maintain the locking pin within the locking recess.

Figure 1A:
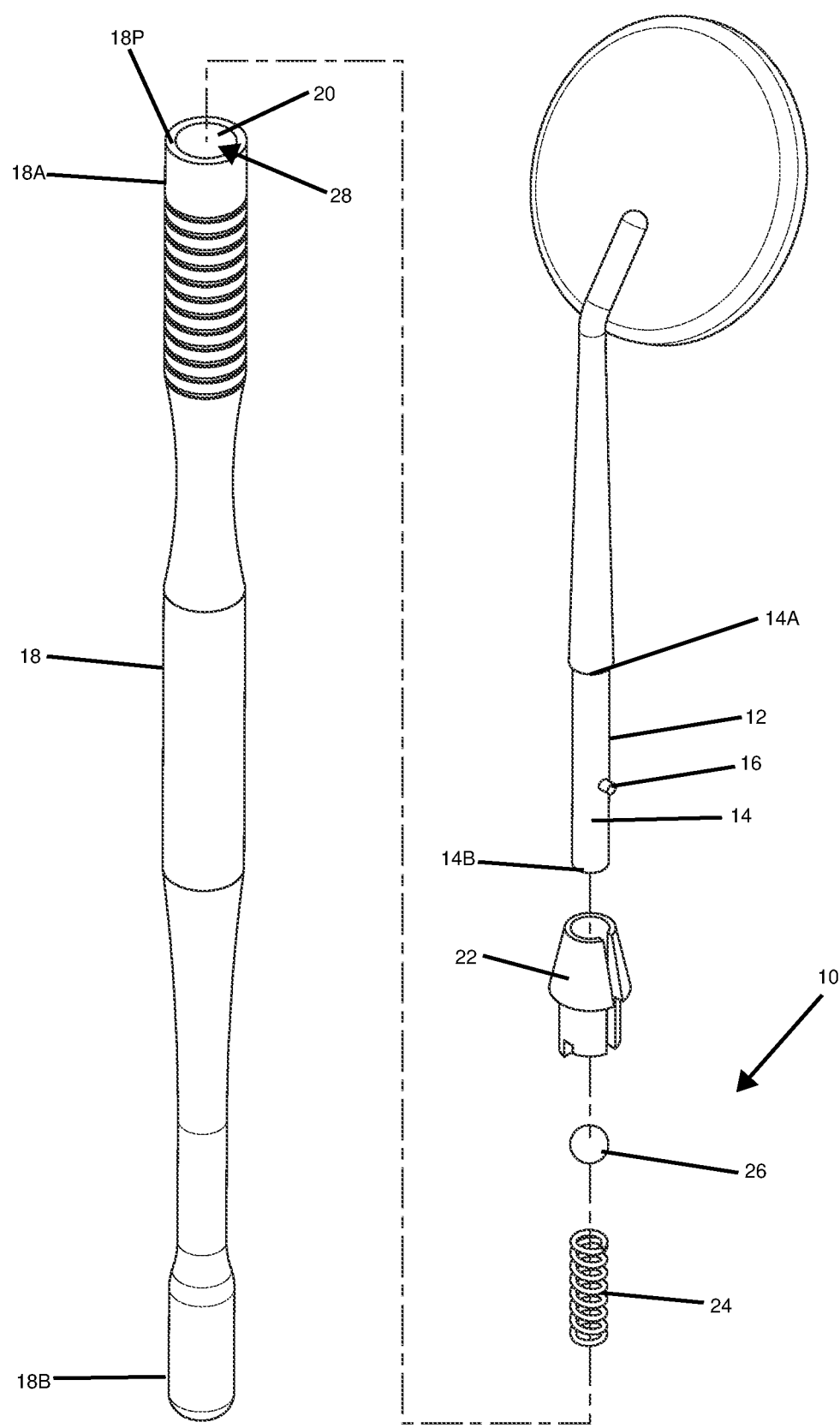
FIG. 1A shows a front exploded view of the quick release mechanism according to one embodiment of the present disclosed technology.
Figure 1B:
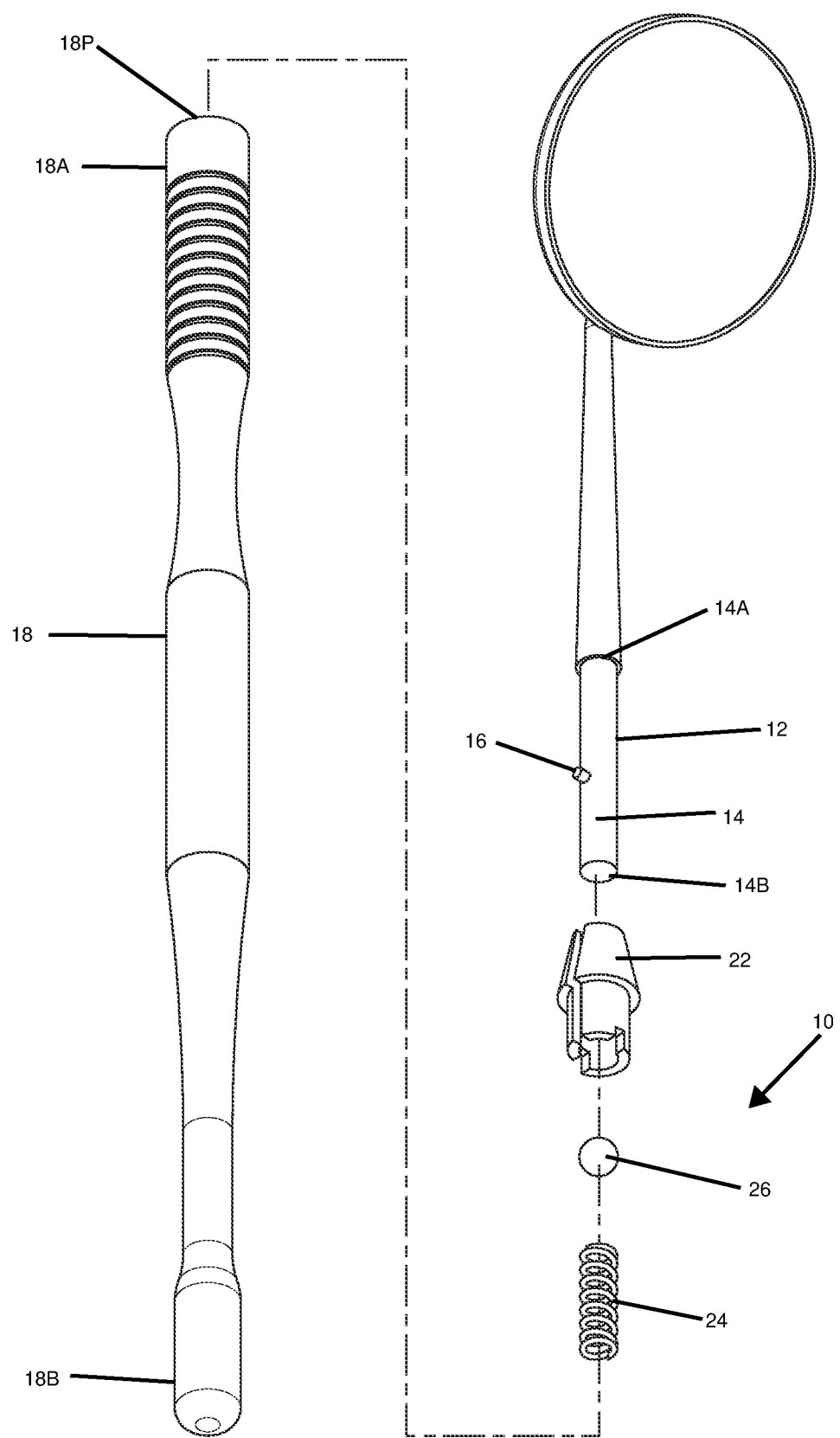
FIG. 1B shows a rear exploded view of the quick release mechanism according to one embodiment of the present disclosed technology.

Referring to FIG. 1A and FIG. 1B, simultaneously, FIG. 1A shows a front exploded view of the quick release mechanism according to one embodiment of the present disclosed technology. FIG. 1B shows a rear exploded view of the quick release mechanism according to one embodiment of the present disclosed technology. The present disclosed technology provides a quick release mechanism 10 comprising a male member 12 including an elongated shaft 14 and a locking pin 16, a female member 18 including a substantially counterbored cavity 20 for receiving the male member 12, a locking joint 22 for receiving the elongated shaft 14 and the locking pin 16 within the female member 18, a spring 24 for securing the locking pin 16 within the locking joint 22, and a bearing 26 for enabling rotation of the elongated shaft 14 within the counterbored cavity 20 with respect to the spring 24.

The elongated shaft 14 of the male member 12 includes a first end 14A, a second end 14B opposite the first end 14A, and a longitudinal length extending between the first end 14A and the second end 14B. The locking pin 16 protrudes substantially orthogonally outwardly from the elongated shaft 14. In embodiments, the locking pin 16 is positioned on the elongated shaft 14 midway between the first end 14A and the second end 14B.

The female member 18 includes a first end 18A, a second end 18B opposite the first end 18A. The first end 18A including a perimeter edge 18P defining an opening 28 providing access to the counterbored cavity 20.

Figure 2A:
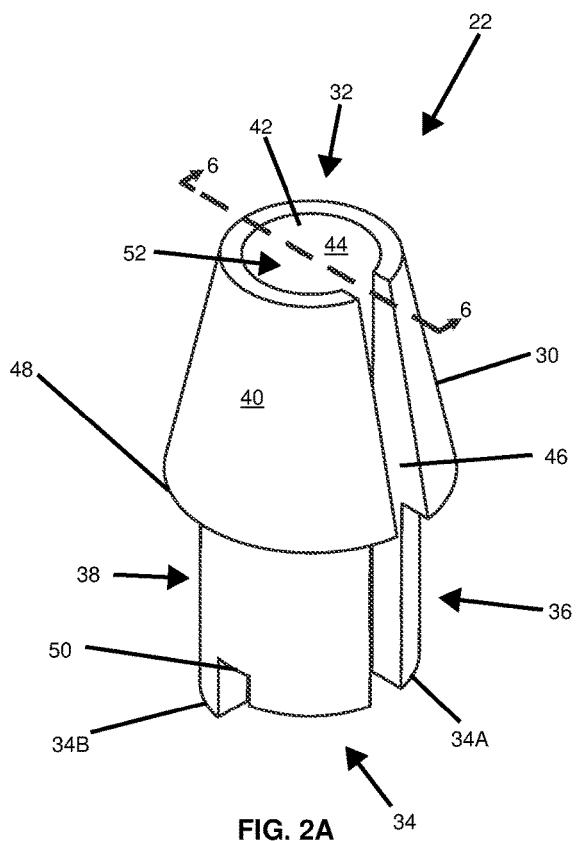
FIG. 2A shows top perspective view of the locking joint of the quick release mechanism according to one embodiment of the present disclosed technology.
Figure 2B:
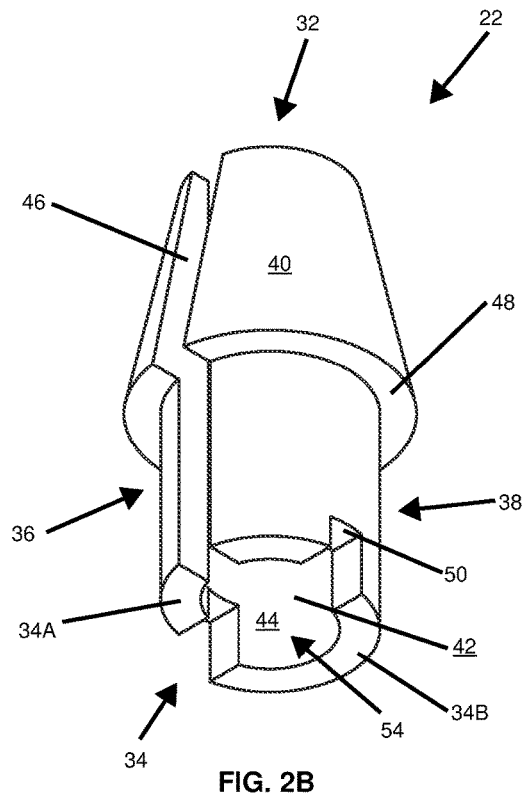
FIG. 2B shows a bottom perspective view of the locking joint of the quick release mechanism according to one embodiment of the present disclosed technology.
Figure 2C:
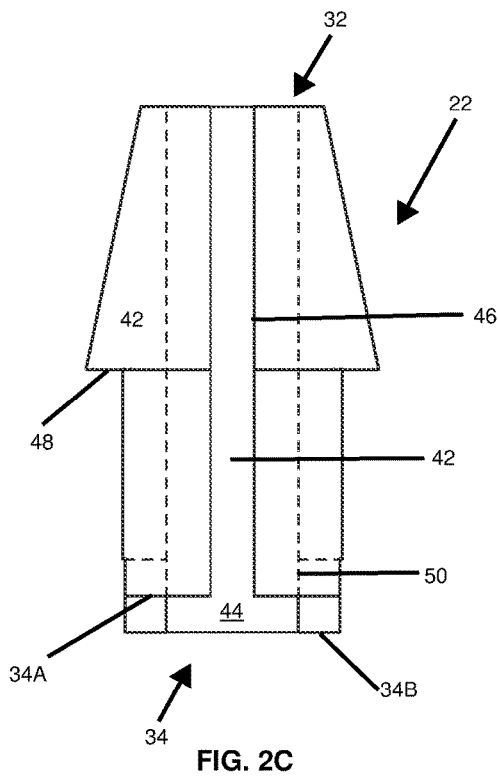
FIG. 2C shows a side elevation view of the locking joint of the quick release mechanism according to one embodiment of the present disclosed technology.
Figure 2D:
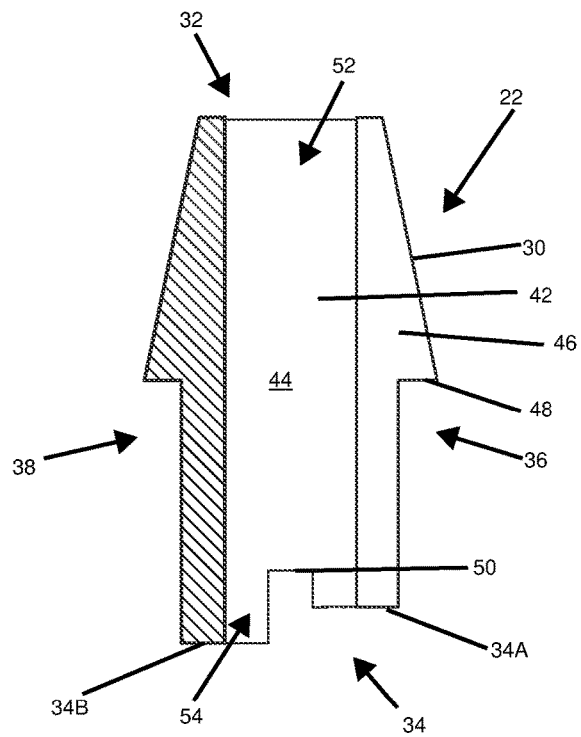
FIG. 2D shows a cross-sectional view of the locking joint of the quick release mechanism along the line 6-6 of FIG. 6A according to one embodiment of the present disclosed technology.

Referring now to FIG. 2A, FIG. 2B, FIG. 2C, and FIG. 2D, simultaneously, FIG. 2A shows top perspective view of the locking joint of the quick release mechanism according to one embodiment of the present disclosed technology. FIG. 2B shows a bottom perspective view of the locking joint of the quick release mechanism according to one embodiment of the present disclosed technology. FIG. 2C shows a side elevation view of the locking joint of the quick release mechanism according to one embodiment of the present disclosed technology. FIG. 2D shows a cross-sectional view of the locking joint of the quick release mechanism along the line 6-6 of FIG. 6A according to one embodiment of the present disclosed technology.

The locking joint 22 includes a body 30 having a first end 32, a second end 34 opposite the first end 32, a first side 36, a second side 38 opposite the first side 36, an exterior surface 40, a longitudinal bore 42 extending from the first end 32 to the second end 34, an interior surface 44 within the longitudinal bore 42, a longitudinal slit 46 disposed on the first side 36, a collar 48 protruding outwardly from the exterior surface 40 of the body 30, a locking recess 50 configured to receive the locking pin 16 therein.

The longitudinal slit 46 extends longitudinally from the first end 32 to the second end 34 and transversely from the exterior surface 40 to the interior surface 44. The longitudinal bore 42 extends entirely through the length of the body 30 defining an entry point 52 at the first end 32 and an exit point 54 at the second end 34. The longitudinal bore 42 is configured to receive the elongated shaft 14 of the male member 12 therethrough while the longitudinal slit 46 is sized and configured to receive the locking pin 16 therethrough.

The second side 38 of the body 30 includes a length greater than a length of the first side 36 of the body 30 such that the second end 34 of the body 30 includes a first peripheral edge 34A on the first side 36 and a second peripheral edge 34B on the second side 38 that is stepped with respect to the first peripheral edge 34A. The locking recess 50 is disposed between the first peripheral edge 34A and the second peripheral edge 34B. In embodiments, the locking recess 50 includes a pair of locking recesses 50A, 50B disposed at each end of the first peripheral edge 34A between each end of the second peripheral edge 34A. In embodiments, the collar 48 tapers in diameter toward the first end of the locking joint 22.

Figure 3A:
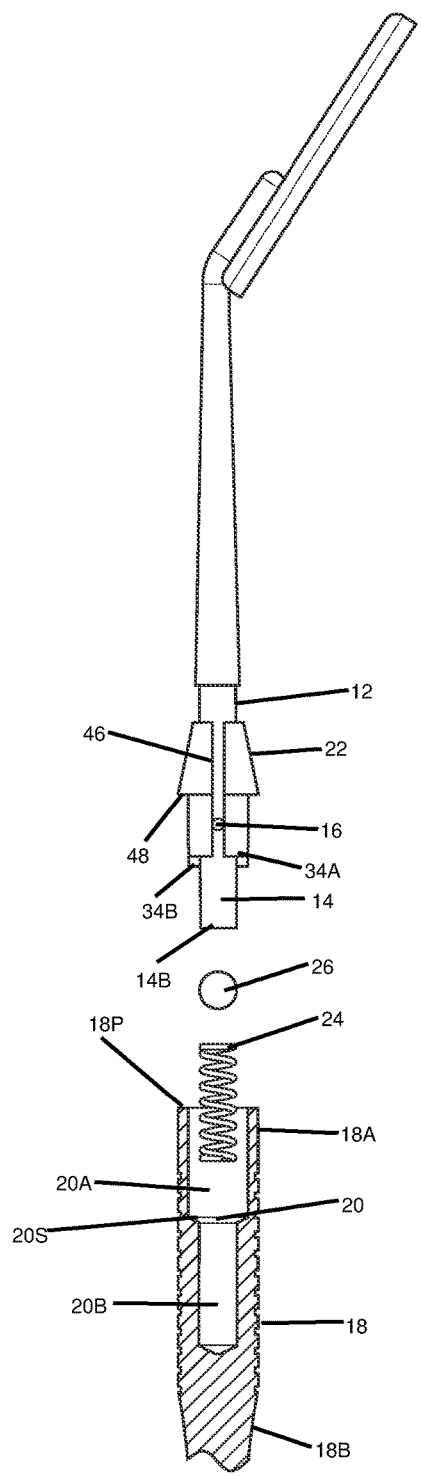
FIG. 3A shows a partial exploded and cross-sectional side view of the quick release mechanism according to one embodiment of the present disclosed technology.
Figure 3B:
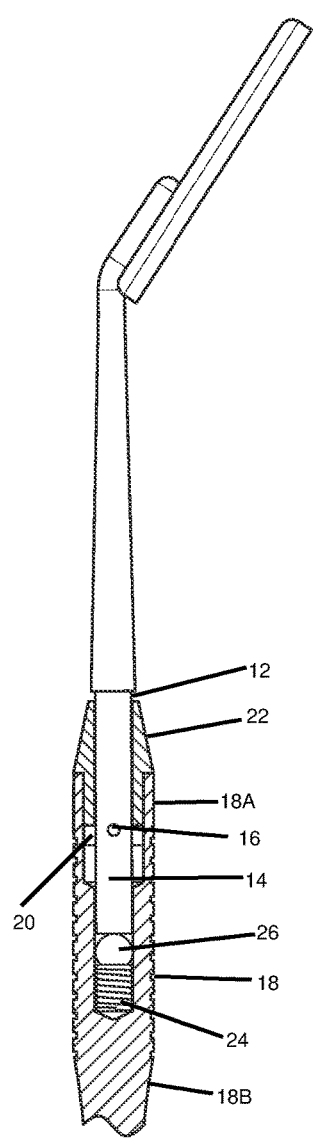
FIG. 3B shows a partial cross-sectional side view of the quick release mechanism according to one embodiment of the present disclosed technology.
Figure 3C:
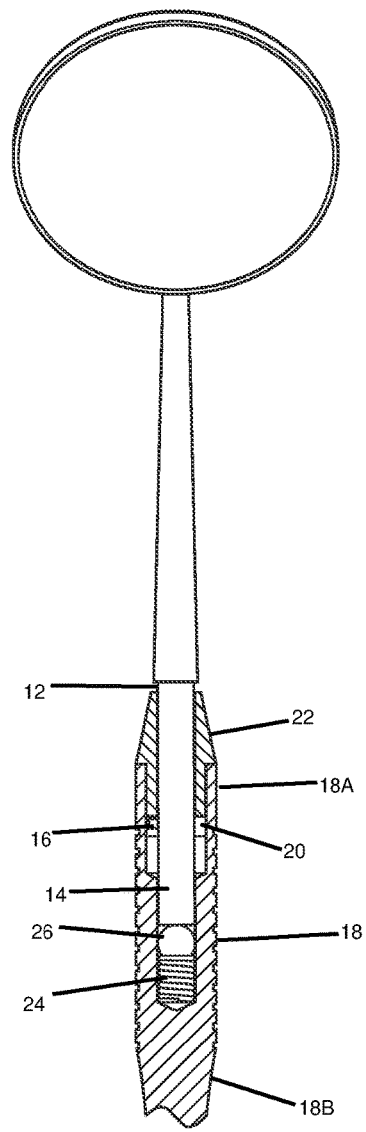
FIG. 3C shows a partial cross-sectional front view of the quick release mechanism according to one embodiment of the present disclosed technology.
Figure 4A:
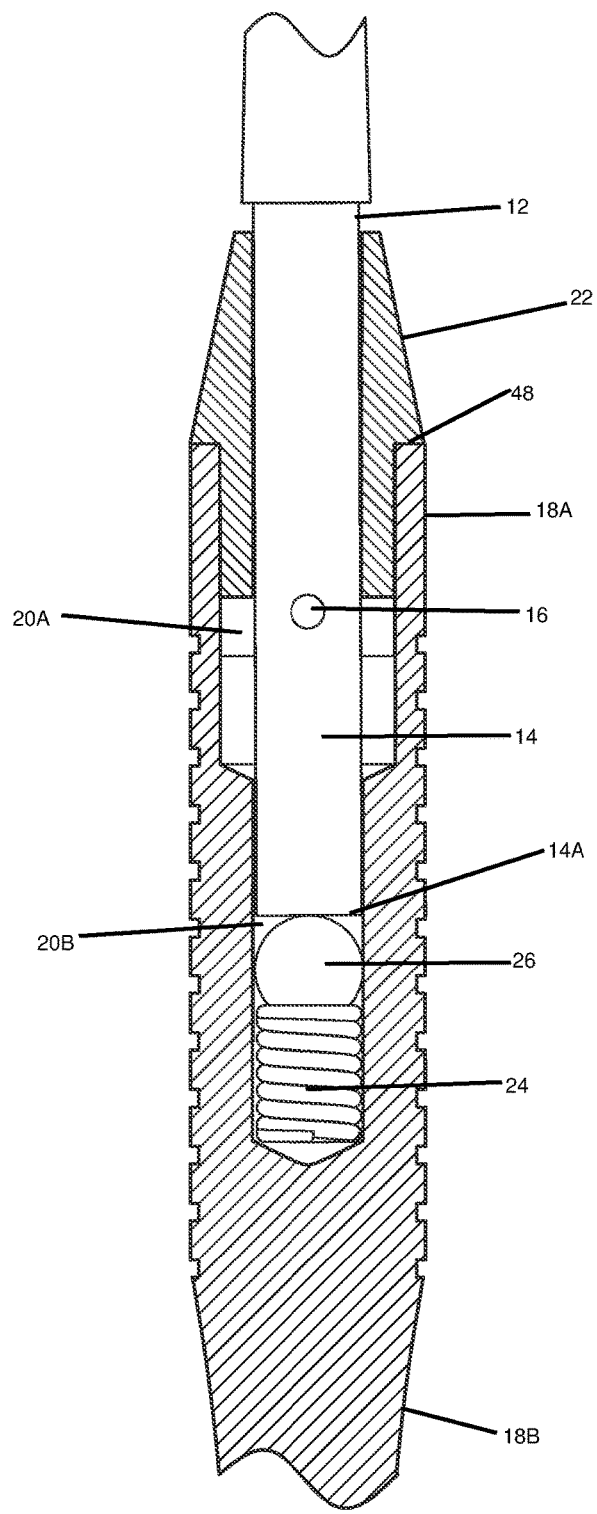
FIG. 4A shows a close-up, partial cross-sectional side view of the quick release mechanism according to one embodiment of the present disclosed technology.
Figure 4B:
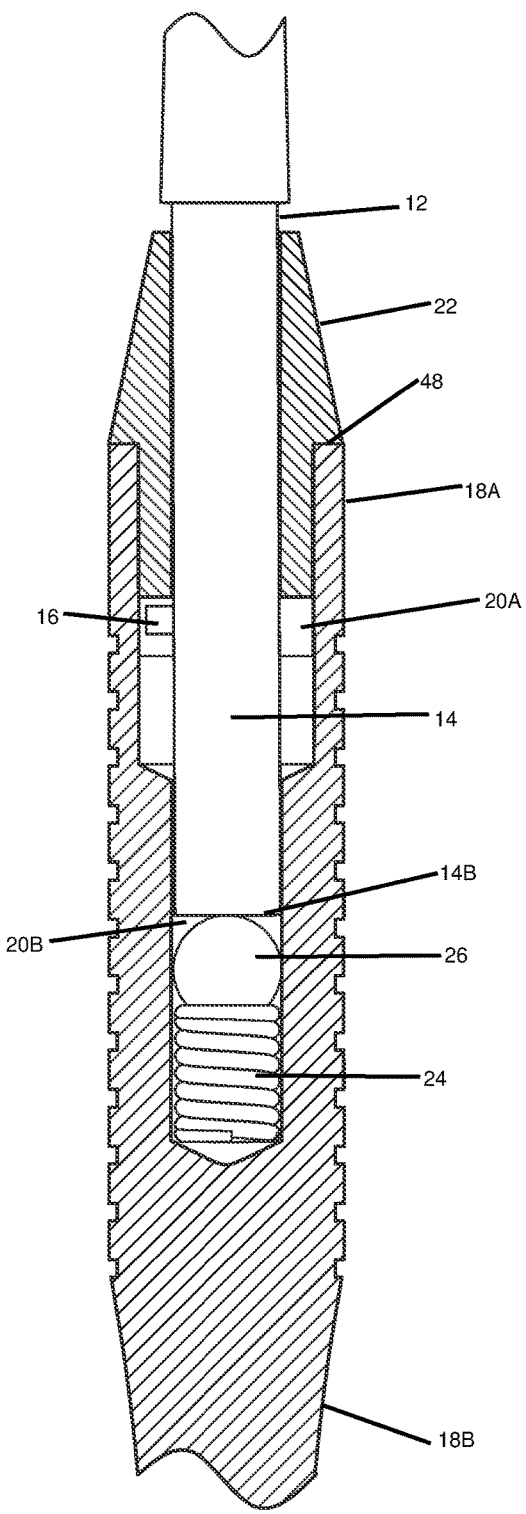
FIG. 4B shows a close-up, partial cross-sectional front view of the quick release mechanism according to one embodiment of the present disclosed technology.
Figure 5:
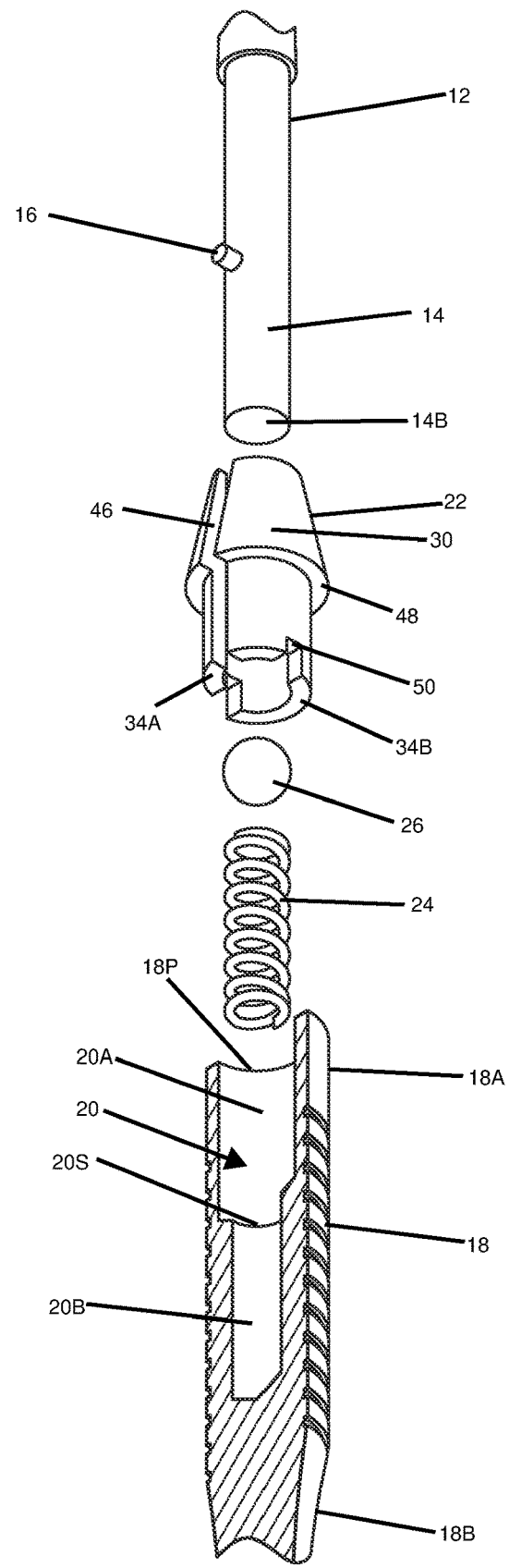
FIG. 5 shows a close-up, exploded view of the quick release mechanism according to one embodiment of the present disclosed technology.
Figure 6:
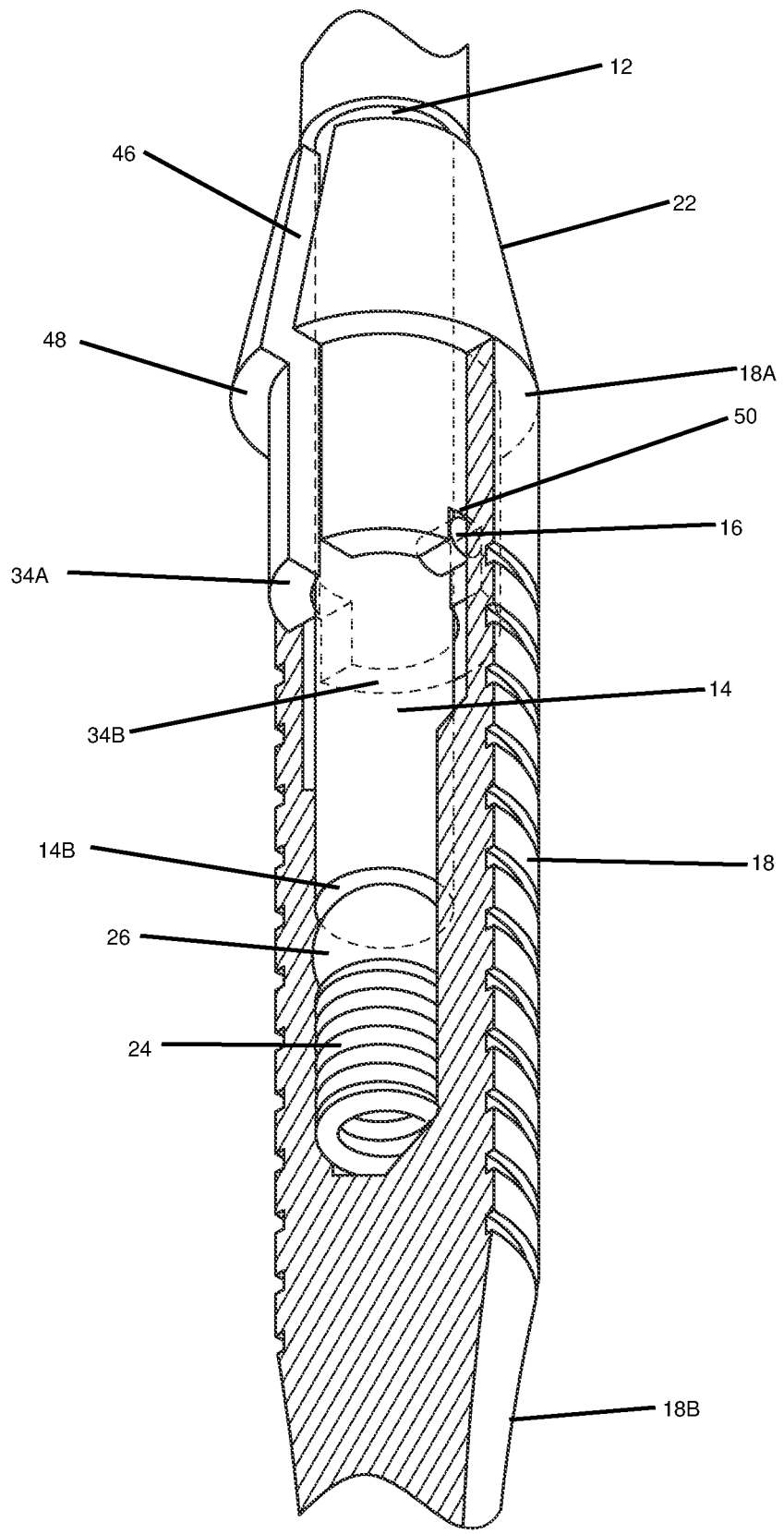
FIG. 6 shows a close-up, partial cross-sectional and phantom perspective view of the quick release mechanism according to one embodiment of the present disclosed technology.

Referring now to FIG. 3A, FIG. 3B, FIG. 3C, FIG. 4A, FIG. 4B, and FIG. 5, simultaneously, FIG. 3A shows a partial exploded and cross-sectional side view of the quick release mechanism according to one embodiment of the present disclosed technology. FIG. 3B shows a partial cross-sectional side view of the quick release mechanism according to one embodiment of the present disclosed technology. FIG. 3C shows a partial cross-sectional front view of the quick release mechanism according to one embodiment of the present disclosed technology. FIG. 4A shows a close-up, partial cross-sectional side view of the quick release mechanism according to one embodiment of the present disclosed technology. FIG. 4B shows a close-up, partial cross-sectional front view of the quick release mechanism according to one embodiment of the present disclosed technology. FIG. 5 shows a close-up, exploded view of the quick release mechanism according to one embodiment of the present disclosed technology. FIG. 6 shows a close-up, partial cross-sectional and phantom perspective view of the quick release mechanism according to one embodiment of the present disclosed technology.

The counterbored cavity 20 includes a first bore 20A with a bottom surface 20S including a second bore 20B. The first bore 20A is coaxial with the second bore 20B and includes a diameter larger than a diameter of the second bore 20B.

The locking joint 22 is attached to the first end 18A of the female member 18. The collar 48 engages the perimeter edge 18P of the first end 18A of the female member 18 to maintain the locking joint 22 at the first end 18A. The second end 34 of the locking joint 22 positioned within the counterbored cavity 20 of the female member 18. In embodiments, the second 34 is positioned against the bottom surface 20S of the counterbored cavity. In some embodiments, the second peripheral edge 34B is the only part of the second end 34 of the locking joint 22 that contacts the bottom surface 20S of the counterbored cavity 20. In embodiments, the longitudinal bore 42 of the locking joint 22 is substantially equal in diameter to the second bore 20B of the counterbored cavity 20.

The spring 24 is disposed within the second bore 20B of the counterbored cavity 20 of the female member 18 in its equilibrium position. The spring 24 is biased toward the first end 18A of the female member 18 such that when displaced from its equilibrium position toward the second end 18B of the female member 18 by the elongated shaft 14 of the male member 12, the spring 24 compresses, developing a potential restoring force toward the first end 18A that may act on the elongated shaft 14 and locking pin 16 when the male member 12 is released. In this way, the spring 24 may secure the locking pin 16 within the locking recess 50 of the locking joint 22. The diameter of the elongated shaft 14 is smaller than the diameter of the second bore 20B of the counterbored cavity 20 to enable the elongated shaft to slide into the second bore 20B and compress the spring 24.

In embodiments, the spring 24 includes a length substantially equal to the length of the second bore 20B. The diameter of the elongated shaft 14 is smaller than the diameter of the second bore 20B of the counterbored cavity 20 enabling the elongated shaft 14 to slide into the second bore 20B when compressing the spring 24 therewith. The locking pin 16 includes a length substantially equal to a length of the width of the body 30 of the locking joint 22 to enable it to be captured by the locking recess 50 of the locking joint 22. The locking pin 16 includes a length that acts as a stop preventing the elongated shaft 14 from going to far into the second bore 20B.

The bearing 26 is positioned on the spring 24 within the counterbored cavity 20. The bearing 26 receives the second end 14B of the elongated shaft 14 thereon and enables rotation of the elongated shaft 14 within the counterbored cavity 20 with respect to the spring 24. In embodiments, the bearing 26 comprises a ball detent for reducing friction and facilitating smooth rotation the shaft when interested therein.

In operation, to secure the male member 12 to the female member 18, first the male member 12 is inserted into the female member 18 by aligning the elongated shaft 14 with the longitudinal bore 42 of the locking joint 22 and the locking pin 16 with the longitudinal slit 46 of the locking joint 22 at the entry point 52.

Next, the elongated shaft 14 is guided into the longitudinal bore 42 and the locking pin 16 is guided into the longitudinal slit 46 and driven toward the second end 18B of the female member 18. As the elongated shaft 14 is driven further into the longitudinal bore 42 of the locking joint 22 and the counterbored cavity 20 of the female member 18, the second end 14B of the elongated shaft 14 contacts the bearing 26, which compresses the spring 24 in the second bore 20B toward the second end 18B of the female member 18. This in turn generates a potential restoring force in the spring 24 that is biased toward the first end 18A of the female member 18. The elongated shaft is driven until the elongated shaft 14 exits the exit point 54 of the locking joint 22 and the locking pin 16 is released from the longitudinal slit 46 into the first bore 20A of the counterbored cavity 20. In this way, the locking pin 16 may shift transversely along the first peripheral edge 34A.

Next, the elongated shaft 14 is rotated to shift the locking pin 16 transversely along the first peripheral edge 34A until the locking pin 16 slips into the locking recess 50. Note, once the locking pin 16 exits the longitudinal slit 46, there is no need to drive the elongated shaft 14 toward the second end 18B of the female member 18 while rotating the elongated shaft 14 to compress the spring 24, because the locking pin may now move freely about the first peripheral edge 34A until it slips into the locking recess 50.

Lastly, once the locking pin 16 slips into the locking recess 50, the elongated shaft 14 is released to lock the male member 12 within the female member 18. Once, the elongated shaft is released, the spring 24 exerts a restoring force onto the second end 14B of the elongated shaft 14 via the bearing 26 to maintain the locking pin 16 within the locking recess 50 and the elongated shaft 14 within the counterbored cavity 20. The spring 24 remains partially compressed when the locking pin 16 is within the locking recess 50, thereby continuously exerting its restoring force on the locking pin 16 and maintaining the locking pin within the locking recess 50.

To release the male member 12 from the female member 18, first the elongated shaft 14 is driven back toward the second end 18B of the female member 18 to compress the spring 24 and disengage the locking pin 16 from the locking recess 50. Next, the elongated shaft 14 is rotated to shift the locking pin 16 transversely back along the first peripheral edge 34A until the locking pin 16 is aligned with the longitudinal slit 46. Lastly, the locking pin 16 and elongated shaft 14 are guided back along the longitudinal slit 44 and longitudinal bore 42, respectively, toward the first end 32 of the locking joint 22 until the locking pin 16 exits the entry point 52 of the locking joint 22. Note, once the locking pin 16 is released from the locking recess 50, there is no need to drive the elongated shaft 14 toward the second end 18B of the female member 18 to compress the spring 24, because the locking pin may now move freely along the first peripheral edge 34A while rotating the elongated shaft 14 to align the locking pin with the longitudinal slit 46.

Figure 7C:
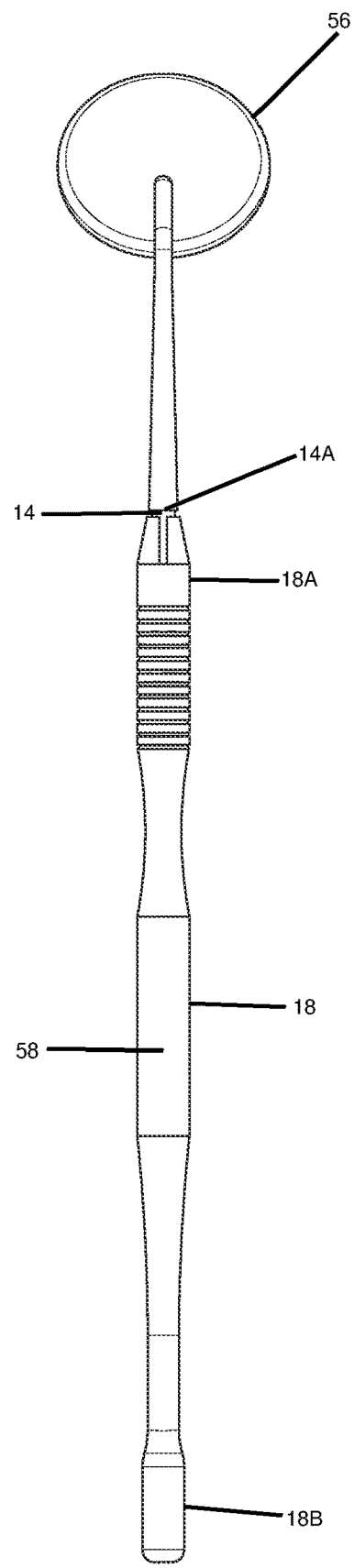
FIG. 7C shows a rear view of the quick release mechanism according to one embodiment of the present disclosed technology.
Figure 7D:
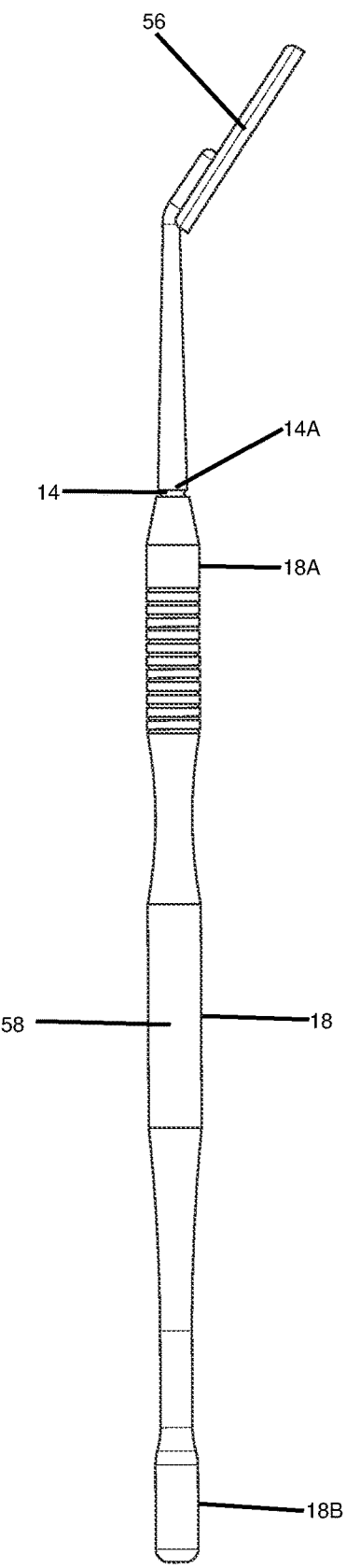
FIG. 7D shows a side view of the quick release mechanism according to one embodiment of the present disclosed technology.

Referring now to FIG. 7A, FIG. 7B, FIG. 7C, and FIG. 7D, simultaneously, FIG. 7A shows a perspective view of the quick release mechanism according to one embodiment of the present disclosed technology. FIG. 7B shows a front view of the quick release mechanism according to one embodiment of the present disclosed technology. FIG. 7C shows a rear view of the quick release mechanism according to one embodiment of the present disclosed technology. FIG. 7D shows a side view of the quick release mechanism according to one embodiment of the present disclosed technology. In embodiments, the first end 14A of the elongated shaft 14 includes a dental tool 56 while the female member 18 includes an elongated handle 58 extending between the first end 18A and the second end 18B of the female member. In some embodiments, the dental tool 56 may be selected from the group consisting of a mouth mirror, sickle probe, scaler, saliva ejector, suction device, dental drill, and dental syringe.

Any device or step to a method described in this disclosure can comprise or consist of that which it is a part of, or the parts which make up the device or step. The term "and/or" is inclusive of the items which it joins linguistically and each item by itself.

For purposes of this disclosure, the term "substantially" is defined as "at least 95% of" the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been disclosed with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

What is claimed is:

1. A quick release locking mechanism, comprising:
   a male member including an elongated shaft having a first end, a second end, the first end opposite the second end, and a longitudinal length extending between the first end and the second end, the elongated shaft including a locking pin protruding substantially orthogonally outwardly from the elongated shaft;
   a female member including a first end, a second end, the first end opposite the second end, and a substantially counterbored cavity configured to receive the elongated shaft of the male member, the first end including a perimeter edge defining an opening providing access to the counterbored cavity, the counterbored cavity comprising a first bore with a bottom surface including a second bore;

a locking joint attached to the first end of the female member, the locking joint including a body having a first end, a second end, the first end opposite the second end, a first side, a second side, the first side opposite the second side, an exterior surface, a longitudinal bore extending from the first end to the second end, an interior surface within the longitudinal bore, a longitudinal slit disposed on the first side, the longitudinal slit extending longitudinally from the first end to the second end and transversely from the exterior surface to the interior surface, and a collar protruding outwardly from the exterior surface of the body, the longitudinal bore configured to receive the male member therethrough while the longitudinal slit is configured to receive the locking pin therethrough, the longitudinal bore defining an entry point at the first end and an exit point at the second end, the collar engaging the perimeter edge of the first end of the female member to maintain the locking joint at the first end of the female member, the second end of the body positioned within the counterbored cavity of the female member, the second side including a length greater than a length of the first side such that the second end includes a first peripheral edge on the first side and a second peripheral edge on the second side that is stepped with respect to the first peripheral edge, the locking joint further including a locking recess disposed between the first peripheral edge and the second peripheral edge, the locking recess configured to receive the locking pin therein;

a spring disposed in the second bore of the counterbored cavity of the female member, the spring biased toward the first end of the female member to secure the locking pin within the locking recess; and a bearing positioned on the spring within the counterbored cavity, the bearing configured to contact the second end of the elongated shaft and enable rotation of the elongated shaft within the counterbored cavity with respect to the spring;

wherein:

the male member removably engages the female member by inserting the elongated shaft into the entry point and the locking pin into the longitudinal slit and compressing the spring until the elongated shaft exits the exit point and the locking pin is released from the longitudinal slit into the counterbored cavity enabling shifting of the locking pin along the first peripheral edge until the locking pin engages the locking recess; and the spring exerts a restoring force onto the second end of the elongated shaft via the bearing to maintain the locking pin within the locking recess.

2. The quick release mechanism of claim 1, wherein the male member is inserted into the female member by aligning the locking pin with the longitudinal slit of the locking joint at the entry point and guiding the elongated shaft into the longitudinal bore and the locking pin into the longitudinal slit toward the second end of the female member.

3. The quick release mechanism of claim 2, wherein the locking pin is released from the longitudinal slit within the first bore of the counterbored cavity of the female member by guiding the locking pin along the longitudinal slit toward the second end of the female member until the locking pin reaches the first peripheral edge of the second end of the locking joint and exits the longitudinal slit at the exit point enabling transverse movement within the first bore along the first peripheral edge toward the locking recess.

4. The quick release mechanism of claim 3, wherein as the elongated shaft is driven further into the longitudinal bore of the locking joint and the counterbored cavity of the female member, the second end of the elongated shaft engages the bearing which compresses the spring in the second bore toward the second end of the female member, thereby generating a potential restoring force in the spring that is biased toward the first end of the female member.

5. The quick release mechanism of claim 4, wherein once the locking pin is released from the longitudinal slit, the locking pin engages the locking recess by rotating the elongated shaft to shift the locking pin toward the second peripheral edge until the locking pin engages the locking recess and then releasing the elongated shaft.

6. The quick release mechanism of claim 5, wherein when the elongated shaft is released, the spring exerts its restoring force on the elongated shaft and the locking pin toward the first end of the female member, thereby securing the pin within the locking recess and locking the male member inside of the female member.

7. The quick release mechanism of claim 6, wherein the spring remains partially compressed when the locking pin is within the locking recess, thereby continuously exerting its restoring force on the locking pin and maintaining the locking pin within the locking recess.

8. The quick release mechanism of claim 7, wherein the male member is released from the female member by driving the elongated shaft back toward the second end of the female member to compress the spring and disengage the locking pin from the locking recess, rotating the elongated shaft to shift the locking pin back along the first peripheral edge to align the locking pin with the longitudinal slit of the locking joint, and guiding the locking pin back along the longitudinal slit toward the first end of the locking joint until the locking pin exits the locking joint.

9. The quick release mechanism of claim 1, wherein the quick release mechanism of claim 1, wherein the first bore is coaxial with the second bore and includes a diameter larger than a diameter of the second bore.

10. The quick release mechanism of claim 1, wherein the second peripheral edge of the locking joint contacts the bottom surface of the counterbored cavity.

11. The quick release mechanism of claim 1, wherein the collar tapers in diameter toward the first end of the locking joint.

12. The quick release mechanism of claim 1, wherein the locking joint further includes a second locking recess disposed between the first peripheral edge and the second peripheral edge, the second locking recess opposite the first locking recess.

13. The quick release mechanism of claim 1, wherein the diameter of the elongated shaft is smaller than the diameter of the second bore of the counterbored cavity enabling the elongated shaft to slide into the second bore when compressing the spring.

14. The quick release mechanism of claim 1, wherein the longitudinal bore of the locking joint is substantially equal in diameter to the second bore of the counterbored cavity.

15. The quick release mechanism of claim 1, wherein the first end of the elongated shaft of the male member includes a dental tool selected from the group consisting of a mouth mirror, sickle probe, scaler, saliva ejector, suction device, dental drill, and dental syringe.

16. The quick release mechanism of claim 1, wherein the female member includes an elongated handle extending between the first end of the female member and the second end of the female member.

\* \* \* \* \*